(12) United States Patent
Loyd

(10) Patent No.: US 6,332,981 B1
(45) Date of Patent: Dec. 25, 2001

(54) ULTRA VIOLET LIQUID PURIFICATION SYSTEM

(76) Inventor: Walter Thomas Loyd, 7451 NW. 7th Ct., Plantation, FL (US) 33317

( * ) Notice: Subject to any disclaimer, the term of this patent is extended or adjusted under 35 U.S.C. 154(b) by 0 days.

(21) Appl. No.: 09/649,623

(22) Filed: Aug. 28, 2000

Related U.S. Application Data
(60) Provisional application No. 60/170,240, filed on Dec. 16, 1999.

(51) Int. Cl.[7] ................................. C02F 1/32; A61L 2/10
(52) U.S. Cl. ..................... 210/198.1; 210/748; 210/169; 422/24; 422/186.3
(58) Field of Search ................................. 210/198.1, 748, 210/169; 422/24, 186.3; 250/436, 437

(56) References Cited

U.S. PATENT DOCUMENTS

| | | | |
|---|---|---|---|
| 1,193,143 | * | 8/1916 | Henri et al. . |
| 2,738,427 | * | 3/1956 | Wagnon . |
| 3,700,406 | * | 10/1972 | Landry . |
| 3,894,236 | * | 7/1975 | Hazelrigg . |
| 4,103,167 | | 7/1978 | Ellner . |
| 4,230,571 | * | 10/1980 | Dadd . |
| 4,255,383 | * | 3/1981 | Schenck . |
| 4,273,660 | * | 6/1981 | Beitzel . |
| 4,274,970 | * | 6/1981 | Beitzel . |
| 4,676,896 | * | 6/1987 | Norton . |
| 4,752,401 | * | 6/1988 | Bodenstein . |
| 4,769,131 | * | 9/1988 | Noll et al. . |
| 4,952,376 | * | 8/1990 | Peterson . |
| 4,969,991 | | 11/1990 | Valadez . |
| 5,178,758 | | 1/1993 | Hwang . |
| 5,230,792 | * | 7/1993 | Sauska et al. . |
| 5,352,359 | * | 10/1994 | Nagai et al. . |
| 5,451,791 | * | 9/1995 | Mark . |
| 5,597,482 | | 1/1997 | Meylon . |
| 5,626,768 | | 5/1997 | Ressler et al. . |
| 5,843,309 | | 12/1998 | Mancil . |
| 5,846,437 | | 12/1998 | Whitby et al. . |
| 5,885,449 | | 3/1999 | Bergmann et al. . |
| 5,916,439 | | 6/1999 | Oleskow . |
| 6,086,760 | * | 7/2000 | Hoffa . |

FOREIGN PATENT DOCUMENTS

95/01307 * 1/1995 (WO) .

* cited by examiner

Primary Examiner—Thomas M. Lithgow

(57) ABSTRACT

Ultra Violet (UV) Light is known to purify fluids without the inclusion of harmful chemicals such as Chlorine, Acid, or other. The known methods to provide the required purification using UV light for a specified volume flow rate utilize (a) varying the length of the chambers and respective light source(s) and/or (b) varying the intensity of the light source. Applicant is disclosing a method of passing the fluid over the light source multiple times by changing the direction of flow, thus maintaining the same intensity and size of the light source. The invention further provides the option to include additional available light sources to increase the total intensity further providing a means to support increased flow. The invention may also utilize a serial swirling motion to increase efficiency.

14 Claims, 4 Drawing Sheets

ULTRA VIOLET LIQUID PURIFICATION SYSTEM

This patent application claims priority to Provisional Patent Application 60/170,240 filed Dec. 16, 1999.

FIELD OF THE INVENTION

This invention relates in general to a method and apparatus for purifying a fluid, more specifically the use of multiple directions of flow of said fluid across the same UV light source(s).

BACKGROUND OF THE INVENTION

Ultra Violet (UV) wavelengths are known to disinfect effluent when the subject fluid is exposed to the UV, with one example being water. The common wavelengths used for purification are 185 nano-meters (nm) and 254 nm. Alternatively an ozone producing source may be used. A collimate UV light source is located within a protective quartz tube sometimes referred to as a sleeve and the fluid is passed through a second, outer chamber located about the quartz sleeve. The UV light source comprises a pair of filaments, a power source, and a translucent housing.

The general equation used for determining UV dose is:

$$D=I*t$$

D=UV Dosage ($mW*s/cm^2$)
I=Intensity (UV Intensity $mW/cm^2$)
t=contact time (seconds)

One skilled in the art recognizes that each design is determined by either of the two variables: time of exposure and intensity.

The present known method for increasing the time of exposure is to increase the length of the associated UV light source (or increase the number of UV lights and quartz sleeves) and the flow chamber. For high volume or high flow rate requirements, the resulting design may be lengthy (generally between 13 and 96 inches). The longer the design, the higher the cost of the UV light source and respective quartz sleeve and outer chamber.

The present known method for increasing dosage is to increase the intensity of each UV light source, increasing the number of UV light sources, or both. The intensity is proportional to the power draw; therefore the greater the intensity, the greater the power consumption.

The use of a swirling motion is currently used in some commercially available UV purification devices.

What is desired is an apparatus to purify various fluids, such as water, whereby the apparatus maintains a reduced footprint, lower manufacturing cost, and power consumption.

SUMMARY OF THE INVENTION

The present invention addresses the deficiencies in the prior art by utilizing a fluid path which exposes the said fluid to the ultra violet (UV) wavelengths.

One aspect of the present invention is the use of an Ultra Violet light source to provide a means to purify various fluids.

A second aspect of the present invention is a means to provide a fluid path, whereby the fluid path exposes the fluid to the same UV light source more than once.

A third aspect of the present invention is a means to transfer the fluid from the first fluid path to the second fluid path.

A fourth aspect of the present invention is a second means to provide a second fluid path, whereby the second fluid path exposes the effluent to the same UV light source. For clarity, the Applicant would like to identify the second fluid path as a change in direction from the first fluid path.

An fifth aspect of the present invention is a means to enclose the UV light source, whereby the means to enclose the UV light source allows the UV light source to purify fluid when the fluid passes proximate to the enclosure and on a second side of the UV light source.

A sixth aspect of the present invention utilizes the means to provide a fluid path, further comprising a means to provide a swirling motion.

A seventh aspect of the present invention further utilizes the swirling action to apply a centrifugal force to said effluent, whereby the centrifugal force places the particles in the effluent proximate the UV light source.

A eighth aspect of the present invention is the use of UV light source(s) which produce Ozone.

A ninth aspect of the present invention is the use of at least one of the fluid paths as a means to cool the UV light source.

A tenth aspect of the present invention is the ability to monitor, provide for, and control the fluid flow rates through the apparatus.

A eleventh aspect of the present invention is a mechanism to monitor the temperature of the fluid, chamber, light sources, and/or other components of the apparatus.

An twelfth aspect of the present invention is the inclusion a pressure relief mechanism.

A thirteenth aspect of the present invention is the inclusion of an automatic power control shutdown for the UV light source.

A fourteenth aspect of the present invention is the inclusion an automated means to monitor the system, including intensity, fluid flow rates, temperature, or other control means.

A fifteenth aspect of the present invention is the ability to interconnect multiple units or stages to provide adequate purification needs to support a specified volume flow rate of effluent.

BRIEF DESCRIPTION OF THE DRAWINGS

For the purpose of initially illustrating the invention, a preferred embodiment is described herein. It should be understood, however, that the present invention is not limited to the specific instrumentalities and methods disclosed. It can be recognized that the figures represent one embodiment required to make the apparatus in which persons skilled in the art may make variations upon the apparatus from therein. In the drawing.

DETAILED DESCRIPTION OF THE DRAWING

Figure 1:
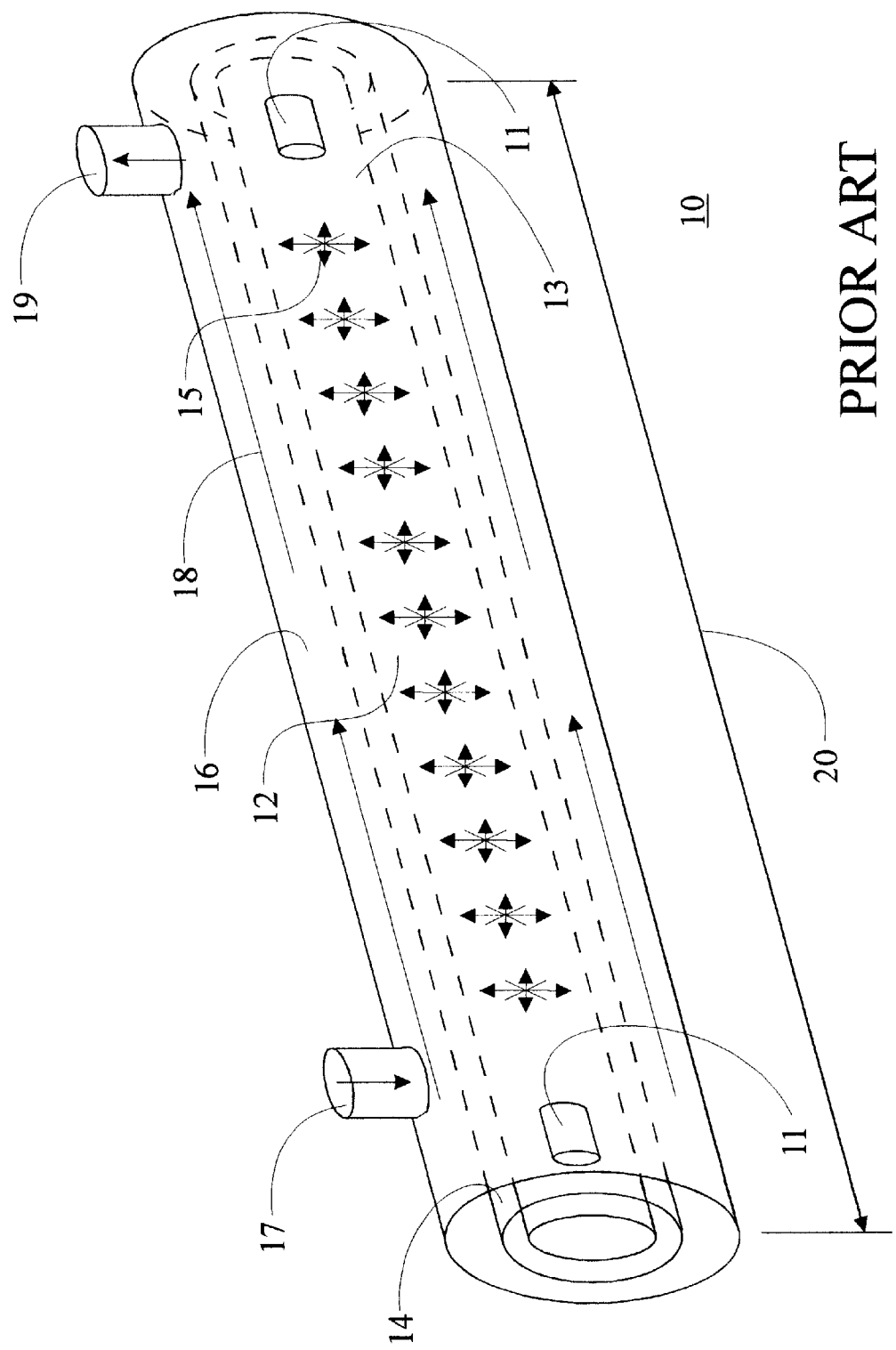
FIG. 1 is an isometric view illustrating the prior art.

FIG. 1 represents an Ultra Violet (UV) fluid purification apparatus 10 in accordance with the prior art. The UV fluid purification apparatus 10 comprises a UV light source 12 such as those produced by Voltarc, GPH620T5L, GSL692T5L and GSL692T5VH used to emit UV wavelengths 15. The UV light source 12 comprises a power source such as those produced by Robertson World Wide, HPSS610 and/or MagneTek TCP000C (not shown), a pair of filaments 11, and a translucent housing 13. The UV light source 12 is generally encased within a fluid impervious housing sometimes referred to as a quartz sleeve 14 such as those produced by General Electric, Type-214. Additional light sources 12 and respective quartz sleeves 14 may be added to increase the intensity. It would be recognized that a power source (not shown) would be required to provide power to the UV light source 12. The fluid impervious housing 14 is located within an outer sleeve 16, whereby the outer sleeve 16 is to provide a fluid flow path 18. The fluid would enter via a fluid entry coupling 17, be transferred along the fluid flow path 18 as controlled by a fluid flow control system (not shown), and exit via a fluid exit coupling 19. The fluid flow control system would control the volumetric flow of the fluid. The length of the fluid to UV interface area 20 is a key variable in determining the design to meet the capacity requirements of the system. Alternatively, there may be multiple UV light sources 12 and respective sleeves 14 inside the chamber 16. Variables of the design may include the length 20, the quantity of UV light sources 12 and respective sleeves 14, diameter of the chamber 16, flow restriction (not shown) and individual bulb intensity. The flow restriction can be accomplished whereby the fluid exit coupling 19 is smaller in cross sectional area as compared to the fluid entry coupling 17.

Figure 2:
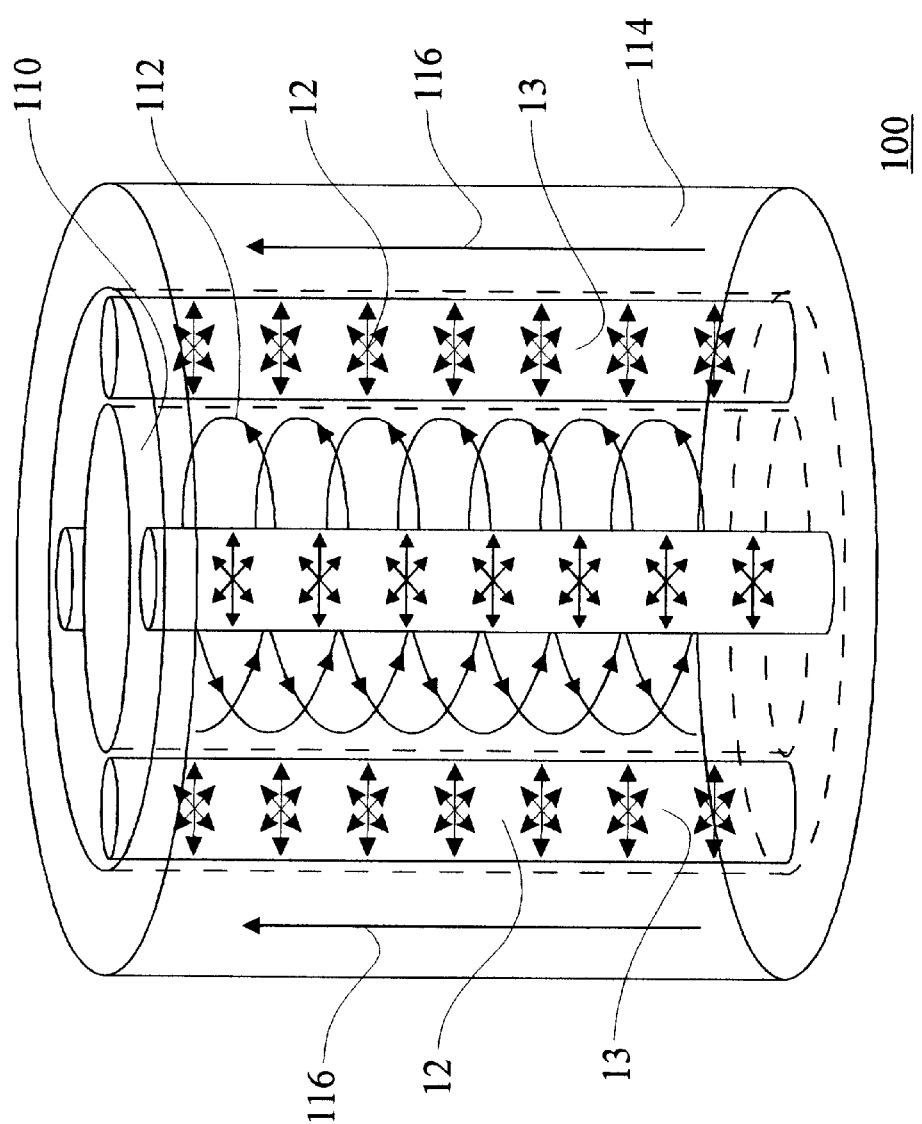
FIG. 2 is an isometric view illustrating the basic principle of a multiple pass UV purification apparatus.

FIG. 2 illustrates a conceptual illustration of a multi-pass UV fluid purification system 100 in accordance with an embodiment of the present invention. At least one, but preferably a plurality UV light sources 12 optionally enclosed within fluid impervious, UV permissive housings (similar to 14 of FIG. 1) would be located proximate a first fluid flow path 112 and a corresponding second fluid flow path 116. The first fluid flow path would be provided by a first fluid flow chamber 110 illustrated herein as located internally proximate the plurality of fluid impervious, UV permissive housings encasing UV light sources 12. The second fluid flow path 116 would be provided by a second fluid flow chamber 114 illustrated herein as located externally proximate the plurality of fluid impervious housings 14 encasing UV light sources 12.

The subject effluent with respective particles would flow along the first fluid flow path 112, preferably in a serial swirling motion (as illustrated). The first fluid flow path 112 further provides a fluid at ambient temperature to the UV light source(s) 12. This is advantageous to the prior art in that the fluid would reach peak temperature at the exiting end of the UV light sources 12, effectively not providing any cooling to that portion of the apparatus. The invention herein provides fluid at both ambient and peak temperature to the UW light source(s) 12 providing even cooling across all locations of the said light source(s) 12.

The subject partially purified fluid would then flow along the second fluid flow path 116, preferably in a serial swirling motion (a linear fluid flow is shown to demonstrate an alternative path). This is advantageous to the prior art in that the fluid is multiply exposed to the same UV light source(s) 12, effectively providing for a fraction of the required length (shown as 20 of FIG. 1) of the apparatus without increasing the intensity of the UV light source(s) 12. This further provides the ability to utilize standard sizes and readily available UV light source(s) thus reducing the cost to the consumer.

The serial swirling motion of the internally located fluid flow 112 provides a centrifugal force (not shown) which forces the heavier particles (not shown) proximate the UV light sources 12 located external to the fluid flow. The serial swirling motion of the externally located fluid flow 116 provides a centrifugal force which remains the lighter particles proximate the UV light sources located internal to the fluid flow. The result is a further efficient apparatus.

Figure 3:
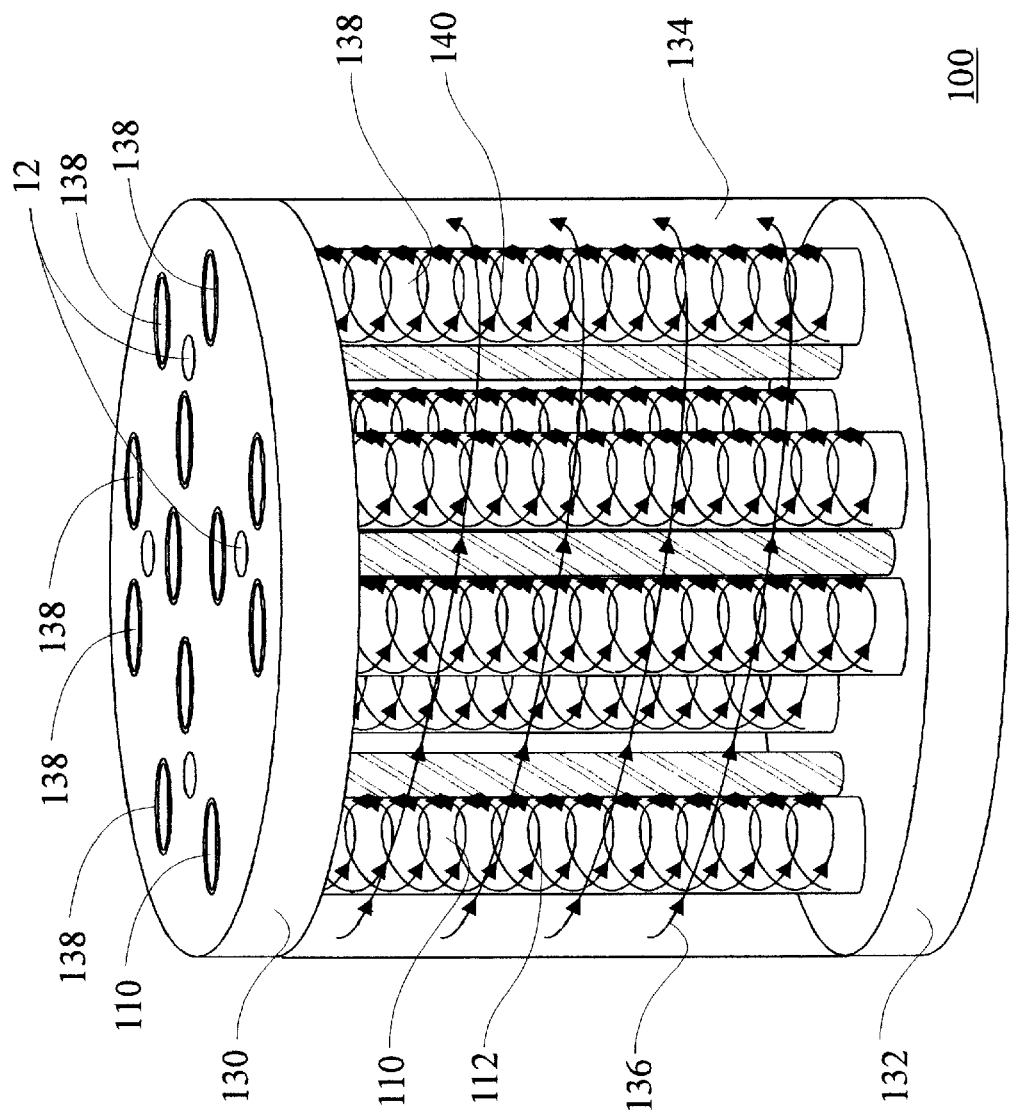
FIG. 3 is an isometric view illustrating a multiple pass UV purification apparatus in accordance with a preferred embodiment.

FIG. 3 illustrates an isometric view of an UV multiple pass purification apparatus 100 in accordance with a preferred embodiment of the present invention. The multiple pass purification apparatus 100 comprises at least one UV light source 12, at least one first fluid flow path 112, and at least a last fluid flow path 136. The first fluid flow path 112 may be confined within a first fluid flow chamber 110. The last fluid flow path 136 may be confined within a last fluid flow chamber 134. The figure introduces multiple fluid flow chambers 138 for multiple fluid flow paths 140. The multiple fluid flow chambers 138 are preferably arranged proximate a UV light source 12. It is further preferred that a last fluid flow path 136 be included to provide additional time of contact to further increase the efficiency of the apparatus. The first fluid flow path 112, the multiple fluid flow paths 140, and the last fluid flow path 136 may be mechanically and/or hydraulically coupled together within a top member 130 and a bottom member 132. It can be recognized that the flow path may be reversed without changing the spirit or intent of the present invention. The reverse flow may provide more evenly distributed cooling to the UV light sources 12. The flow path associated with the preferred embodiment using multiple fluid flow chambers 138 will be described further in FIG. 4. Quartz sleeves (shown as 14 in FIG. 1) may be included to enclose the UV light source(s) 12. A swirling motion as shown may be utilized to further increase the efficiency, but is not necessarily required. Fluid flow restrictions (not shown) may be incorporated. Fluid flow- .generators such as a pump (not shown) may further be incorporated. Filtration devices may be further incorporated, on the entrance, within, and/or exit side of the fluid flow.

Figure 4:
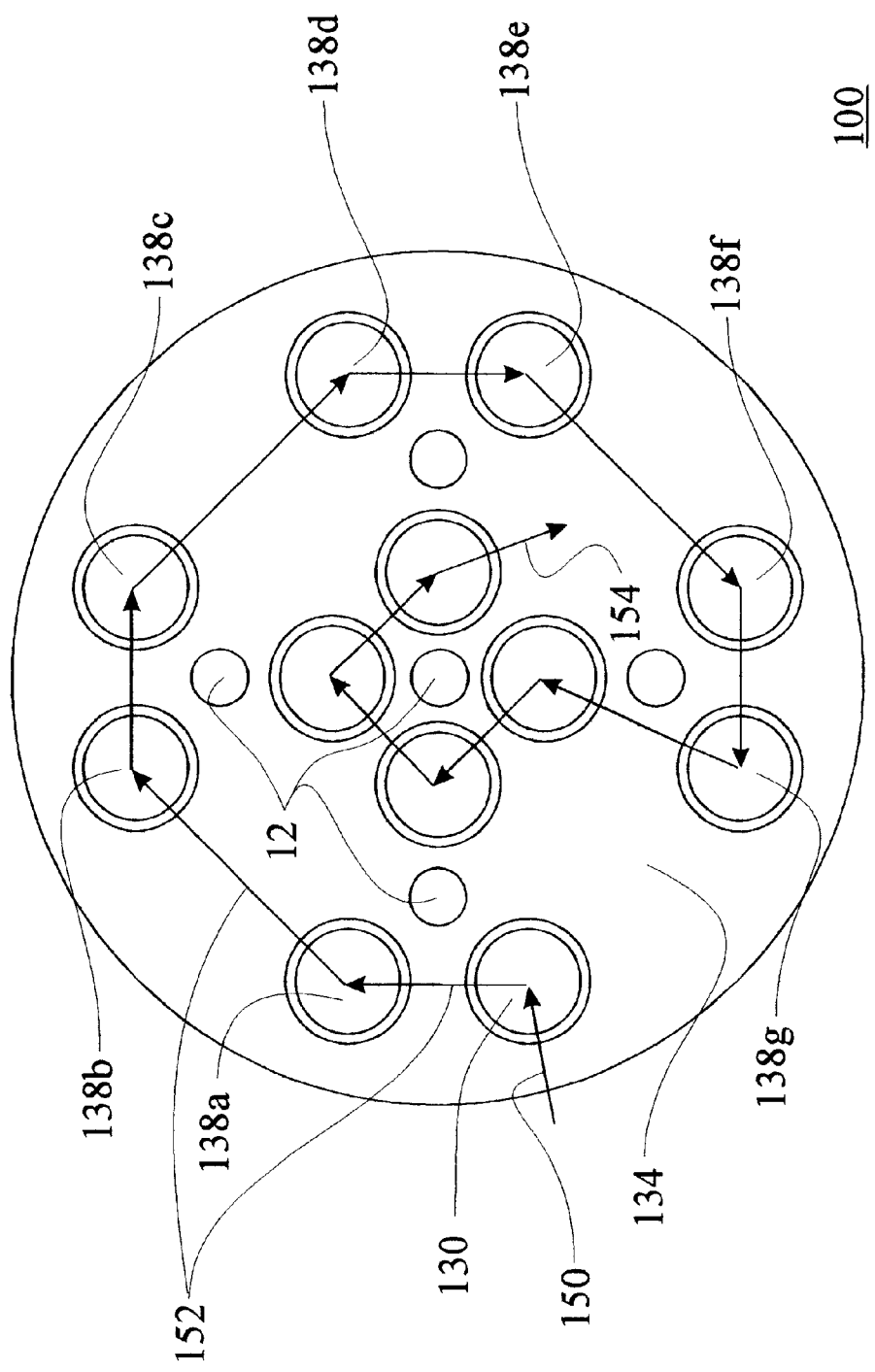
FIG. 4 is a top view of the multiple pass UV purification apparatus of FIG. 3.

FIG. 4 further illustrates the flow of effluent through the multiple pass UV purification apparatus 100. The effluent would enter through an entrance path 150, travel through a first flow path 130, flow along a transfer path 152 transferring to a second flow path 138a, continuing through the transfer path 152 to a third flow path 138b, etc., until the effluent is purified and exits through an exit path 154. The flow would alternate directions, flowing a first direction in the first chamber 130 and in an opposing direction in the next chamber 138a. This would continue for each chamber. The effluent may continue to flow in a last chamber 134 further exposing the effluent to the UV light source(s) 12. Upon completion, the fluid would return to the source through an exit coupling (shown as 19 of FIG. 1).

It can be recognized that the direction of flow, the number of chambers 130, 138, and 134, the respective number of UV light source(s) 12, the physical arrangement, and other variable in design should not limit the spirit or intent of the present invention.

What is claimed:

1. An liquid purification apparatus, the apparatus comprising:

an external housing defining an external chamber;

at least one ultra-violet radiation source located at least partially within the external chamber, and a multi-directional tubular structure having a plurality of tubes located at least partially within the external chamber and defining a first continuous multidirectional flow path within said plurality of tubes and a second flow path outside of said plurality of tubes but within the external housing, means to cause the liquid to flow on said first path through the multi-directional tubular structure and then on said second path external to the multi-directional tubular structure and enclosed within the external housing inside the external chamber wherein the liquid is exposed to the ultraviolet radiation source on both the first and second path.

2. The apparatus of claim 1, whereby the apparatus utilizes a plurality of ultraviolet radiation sources.

3. The apparatus of claim 1, whereby the ultraviolet radiation source is at least one of:
   e) 185 nano-meter wavelength light source
   f) 254 nano-meter wavelength light source
   g) 185–254 nano-meter variable wavelength light source
   h) Ozone producing light source.

4. The apparatus of claim 1, whereby the apparatus further comprises an entry coupling, and an exit coupling.

5. The apparatus of claim 4, whereby the exit coupling has an exit coupling cross sectional area, the entry coupling has an entry coupling cross sectional area, and the exit cross sectional area is differing in size compared to the entry cross sectional area.

6. The apparatus of claim 1, whereby the at least one of the multi-directional tubular structure and the external chamber provides a means to cause liquid to flow in a swirling motion.

7. The apparatus of claim 1, whereby the liquid flow path through the multi-directional tubular structure and external to the multi-directional tubular structure and enclosed within the external chamber is such to provide a means to control the temperature of the ultra-violet radiation source and system.

8. A pool water purification apparatus, the apparatus comprising:
   an external housing defining an external chamber,
   at least one ultra-violet radiation source located at least partially within the external chamber, and
   a multi-directional tubular structure having a plurality of tubes located at least partially within the external chamber and defining a first continuous multidirectional flow path within said plurality of tubes and a second flow path outside said plurality of tubes but within the external housing and at least a portion of the multi-directional tubular structure located proximate at least one ultra-violet radiation source, means to cause said water to flow on said first path; through the multi-directional tubular structure and then on said second path external to the multi-directional tubular structure and enclosed within the external housing inside the external chamber wherein the water is exposed to the ultraviolet radiation source on both the first and second path.

9. The apparatus of claim 8, the apparatus further comprising:
   an entry coupling, and
   an exit coupling.

10. The apparatus of claim 8, whereby at least a portion of the multi-directional tubular structure is of an Ultraviolet permissive material.

11. The apparatus of claim 8, whereby the ultraviolet radiation source is at least one of:
   e) 185 nano-meter wavelength light source
   f) 254 nano-meter wavelength light source
   g) 185–254 nano-meter variable wavelength light source
   h) Ozone producing light source.

12. The apparatus of claim 9, whereby the exit coupling has an exit coupling cross sectional area, the entry coupling has an entry coupling cross sectional area, and the exit cross sectional area is differing in size compared to the entry cross sectional area.

13. The apparatus of claim 9, whereby the at least one of the multi-directional tubular structure and the external chamber provides a means to cause liquid to flow in a swirling motion.

14. The apparatus of claim 1, whereby the multi-directional tubular structure is of an Ultraviolet permissive material.

\* \* \* \* \*